United States Patent
Ferrer Montiel et al.

(10) Patent No.: US 9,079,048 B2
(45) Date of Patent: Jul. 14, 2015

(54) COSMETIC OR DERMOPHARMACEUTICAL COMPOSITION COMPRISING ENKEPHALIN-DERIVED PEPTIDES FOR REDUCING AND/OR ELIMINATING FACIAL WRINKLES

(75) Inventors: Antonio Vincente Ferrer Montiel, Alicante (ES); Juan Cebrián Puche, Barcelona (ES); Arturo Puig Montiel, Barcelona (ES)

(73) Assignee: Lipotec, S.A., Gava, Barcelona (ES)

( * ) Notice: Subject to any disclaimer, the term of this patent is extended or adjusted under 35 U.S.C. 154(b) by 1530 days.

(21) Appl. No.: 11/910,719

(22) PCT Filed: Mar. 29, 2006

(86) PCT No.: PCT/ES2006/000151
§ 371 (c)(1),
(2), (4) Date: Jun. 11, 2008

(87) PCT Pub. No.: WO2006/106164
PCT Pub. Date: Oct. 12, 2006

(65) Prior Publication Data
US 2009/0155317 A1 Jun. 18, 2009

(30) Foreign Application Priority Data
Apr. 8, 2005 (ES) .................................. 200500824

(51) Int. Cl.
*A61K 38/00* (2006.01)
*A61K 8/64* (2006.01)
*A61Q 19/08* (2006.01)
*C07K 14/70* (2006.01)

(52) U.S. Cl.
CPC . *A61Q 19/08* (2013.01); *A61K 8/64* (2013.01); *C07K 14/70* (2013.01); *A61K 38/00* (2013.01)

(58) Field of Classification Search
CPC ......... A61K 38/00; A61K 8/64; A61Q 19/08; C07K 14/70
USPC ............. 514/1.1, 21.6, 21.7, 21.8, 21.9, 18.6, 514/18.8; 424/401, 63, 69
See application file for complete search history.

(56) References Cited

U.S. PATENT DOCUMENTS

| | | | |
|---|---|---|---|
| 6,335,368 B1 | 1/2002 | Liviero et al. | |
| 6,395,513 B1 * | 5/2002 | Foster et al. | 435/69.3 |
| 8,691,566 B1 * | 4/2014 | Zhu et al. | 435/325 |
| 2004/0120918 A1 | 6/2004 | Lintner et al. | |
| 2004/0127556 A1 | 7/2004 | Lu et al. | |
| 2004/0147443 A1 * | 7/2004 | Renault | 514/12 |
| 2005/0036974 A1 * | 2/2005 | Catroux et al. | 424/70.14 |

FOREIGN PATENT DOCUMENTS

| | | | |
|---|---|---|---|
| EP | 0 704 210 | 4/1996 | |
| EP | 1 180 524 | 2/2002 | |
| FR | 2735687 | * 6/1995 | ............... A61K 7/48 |
| FR | 2 746 641 | 10/1997 | |
| FR | 2 798 590 | 3/2001 | |
| FR | 2 809 005 | 11/2001 | |
| FR | 2 838 344 | 10/2003 | |
| FR | 2 845 288 | 4/2004 | |
| FR | 2 846 885 | 5/2004 | |
| FR | 2 8477 250 | 5/2004 | |
| FR | 2 850 573 | 8/2004 | |
| FR | 2 857 588 | 1/2005 | |
| WO | WO 97/34620 | 5/1997 | |
| WO | WO 2004/101609 | 11/2004 | |

OTHER PUBLICATIONS

Choi H-K, Flynn GL, Amidon GL, "Transdermal Delivery of Bioactive Peptides: The Effect of n-Decylmethyl Sulfoxide, pH, and Inhibitors on Enkephalin Metabolism and Transport," Pharmaceutical Research, 1990, 7(11): 1099-1106.*
Wrinkles from www.medicinenet.com, pp. 1-5. Accessed May 5, 2011.*
Machine translation of FR 2735687, pp. 1-2. Accessed May 5, 2011 (published Jun. 21, 1995).*
Water from www.biology-online.org/dictionary/Water, pp. 1-3. Accesssed Apr. 24, 2014.*
International Search Report for International Application No. PCT/ES2006/000151 mailed Jul. 27, 2006.
Albericio et al. "Preparation and Application of the 5-(4-(9-Fluorenylmethyloxycarbonyl)aminomethyl-3-,5-dimethoxyphenoxy)-valeric Acid (PAL) Handle for the Solid-Phase synthesis of C-Terminal Peptide Amides under Mild Conductions." *J. Org. Chem.* vol. 55. 1990. pp. 3730-3743.

(Continued)

*Primary Examiner* — Julie Ha
(74) *Attorney, Agent, or Firm* — Fay Sharpe LLP (57) ABSTRACT

A cosmetic or dermopharmaceutical composition comprising enkephalin-derived peptides of general formula (I) for reducing and/or eliminating facial wrinkles is disclosed. The cosmetic or dermopharmaceutical composition can be applied to the skin, preferably skin of the face, to reduce and/or eliminate facial wrinkles, such facial expression wrinkles.
Use of the peptide of general formula (I) in the preparation of a cosmetic or dermopharmaceutical composition for reducing and/or eliminating facial wrinkles is also disclosed.

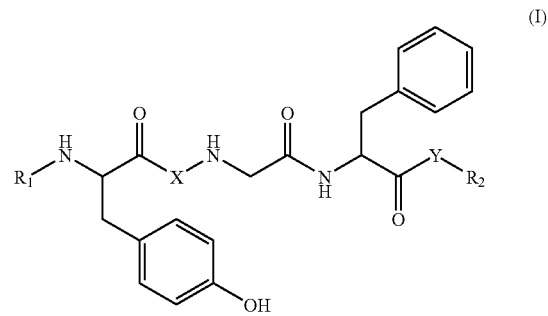

31 Claims, 2 Drawing Sheets (56) References Cited

OTHER PUBLICATIONS

Atherton et al. "Solid Phase Peptide Synthesis." *IRL Press at Oxford University.* 1989 pp. 1-61.

Barlos et al. "Veresterung von partiell geschützten peptid-fragmenten mit harzen. Einsatz von 2-chlortritylchlorid zur synthese von Leu15-gastrin I." *Tetrahedron Letters.* vol. 30. No. 30. 1989. pp. 3947-3950.—English Abstract provided.

Barlos et al. "Darstellung geschützter peptid-fragmente unter einsatz substituierter triphenylmethyl-harze." *Tetrahedron Letters.* vol. 30. No. 30. 1989. pp. 3943-3946.—English Abstract provided.

Bergevin et al. "Presynaptic µ-opioid receptors regulate a late step of the scretory process in rat venral tegmental area GABAergic neurons." *Neuropharmacology.* vol. 42. 2002. pp. 1065-1078.

Blanes-Mira et al. "Small peptides patterned after the N0terminus domain of SNAP25 inhibit SNARE complex assembly and regulated exocytosis." *J. of Neurochemistry.* vol. 88. 2004. pp. 124-135.

Bodanszky et al. "The Practice of Peptide Synthesis: $2^{nd}$ Edition." *Springer Lab Manual. New York.* 1984. pp. 77-126.

Carruthers et al. "Treatment of Glabellar Frown Lines with *C. Botulinum*—A Exotoxin." *J. of Dermatol. Surg. Oncol.* vol. 18. 1992. pp. 17-21.

Faber et al. "Opiods Inhibit Lateral Amygdala Pyramidal Neurons by Enhancing a Dendritic Potassium Current." *J. of Neuroscience.* vol. 24. No. 12. 2004. pp. 3031-3039.

Greene et al. "Protective Groups in Organic Synthesis: 309-404. $2^{nd}$ Edition." *John Wiley & Son. New York.* 1991. pp. 309-404.

Hille. "Ion Channels of Excitable Membranes: Third Edition." *Sinauer Associate Inc. Massachusetts.* 2001. pp. 87-93, pp. 393-396.

Author Unknown. "IUPAC-IUB Joint Commission on Biochemical Nonmenclature (JCBN). Nonmenclature and Symbolism for Amino Acides and Peptides." *Eur. J. Biochem.* vol. 138. 1984. pp. 9-37.

Kaiser et al. "Color Test for Detection of Free Terminal Amino Groups in the Solid-Phase Synthesis of Peptides." *Anal. Biochem.* vol. 34 1969. pp. 595-598.

Kieffer et al. "Exploring the opioid system by gene knockout." *Progress in Neurobiology.* vol. 66. 2002. pp. 285-306.

Kullmann. "Proteases as Catalysts for Enzymic Syntheses of Opioid Peptides." *J. of Biol. Chem.* vol. 255. No. 17. 1980. pp. 8234-8238.

Lloyd-Williams et al. "Chemical Approaches to the Synthesis of Peptides and proteins." *CRC Press. New York.* 1997. pp. 19-93.

Matsueda et al. "A *p*-Methylbenzhydrylamine Resin for Improved Solid-Phase Sytesis of Peptide Amides." *Peptides.* vol. 2. 1981. pp. 45-50.

Mendez-Eastman. "Continuing Education: Boxtox: A Review." *Plastic Surgical Nursing.* vol. 23. No. 2. 2003. pp. 64-69.

Nicol et al. "Tumor Necrosis Factor Enhances the Capsaicin Sensitivity of Rat Sensory Neurons." *J. of Neuroscience.* vol. 17. No. 3. 1997. pp. 975-982.

Rink. "Solid-Phase Synthesis of Protected Peptide Fragments using a Trialkoxy-Diphenyl-Methylester Resin." *Tetrahedron Letters.* vol. 28. No. 33. 1987. pp. 3787-3790.

Stewart. "Solid Phase Peptide Synthesis. $2^{nd}$ Edition." *Pierce Chemical Company, Illinois.* 1984. pp. 1-95.

Wang et al. "*p*-Alkoxybenzyle Alchohol Resin and *p*-Alkoxybenzyloxycarbonylhydrazide Resin for Solid Phase Synthesis of Protected Peptide fragments." *J. of Am. Chem. Soc.* vol. 95. vol. 4. 1973. pp. 1328-1333.

Roberts et al. "Unusual Amino Acids in Peptide Synthesis." *The Peptides.* vol. 5. 1983. pp. 341-449.

Wilkinson et al. "Harry's Cosmeticlogy: Seventh Edition." *George Godwin. Great Britain.* 1982. pp. 50-73, 757-799.

\* cited by examiner

SEQUENCE LISTING

<160> NUMBER OF SEQ ID NOS: 7

<210> SEQ ID NO 1
<211> LENGTH: 206
<212> TYPE: PRT
<213> ORGANISM: Homo sapiens

<400> SEQUENCE: 1

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 2
<211> LENGTH: 84
<212> TYPE: PRT
<213> ORGANISM: Homo sapiens

<400> SEQUENCE: 2

```
Met Ala Glu Asp Ala Asp Met Arg Asn Glu Leu Glu Glu Met Gln Arg
1               5                   10                  15
```

```
Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe

<210> SEQ ID NO 3
<211> LENGTH: 13
<212> TYPE: PRT
<213> ORGANISM: Homo sapiens

<400> SEQUENCE: 3

Glu Leu Glu Glu Met Gln Arg Arg Ala Asp Gln Leu Ala
1               5                   10

<210> SEQ ID NO 4
<211> LENGTH: 8
<212> TYPE: PRT
<213> ORGANISM: Homo sapiens

<400> SEQUENCE: 4

Glu Glu Met Gln Arg Arg Ala Asp
1               5

<210> SEQ ID NO 5
<211> LENGTH: 6
<212> TYPE: PRT
<213> ORGANISM: Homo sapiens

<400> SEQUENCE: 5

Glu Glu Met Gln Arg Arg
1               5

<210> SEQ ID NO 6
<211> LENGTH: 5
<212> TYPE: PRT
<213> ORGANISM: Homo sapiens

<400> SEQUENCE: 6

Tyr Gly Gly Phe Leu
1               5

<210> SEQ ID NO 7
<211> LENGTH: 5
<212> TYPE: PRT
<213> ORGANISM: Homo sapiens

<400> SEQUENCE: 7

Tyr Ala Gly Phe Leu
1               5
```

COSMETIC OR DERMOPHARMACEUTICAL COMPOSITION COMPRISING ENKEPHALIN-DERIVED PEPTIDES FOR REDUCING AND/OR ELIMINATING FACIAL WRINKLES

FIELD OF THE INVENTION

The present invention relates to a cosmetic or dermopharmaceutical composition for application in the skin, preferably in the skin of the face, to reduce and/or eliminate facial wrinkles, preferably facial expression wrinkles. Said composition comprises a cosmetically or dermopharmaceutically effective amount of a peptide of general formula (I), wherein $R_1$ can be H or alkyl, aryl, aralkyl or acyl group, $R_2$ can be amino, hydroxy or thiol, all of them substituted or non-substituted with aliphatic or cyclic groups and X and Y are selected from the group of natural amino acids in their L- or D-form or non-encoded amino acids such as for example citrulline, ornithine, sarcosine, phenylglycine, β-alanine or norleucine, among others.

(I)

BACKGROUND OF THE INVENTION

One of the most visible signs of aging in humans is the changes experienced by the skin: dryness, appearance of spots, flaccidity and wrinkles. These effects can be caused by external agents such as the constant exposure to the sun, atmospheric pollution or the contact with chemical agents present in, for example, cleansing products, but they are also a consequence of intrinsic physiological, biochemical and histological changes in the human organism, due to the decrease in the synthesis of proteins such as collagen or elastin, to an increase in proteolysis, and to a general breaking of the skin barrier, of the connective tissue and of cohesion.

Different active ingredients have been described for preventing and decreasing aging symptoms, such as for example, retinoids, hydroxy acids, flavonoids or derivatives of vitamin C and E. Said compounds normally act by improving skin hydration, increasing cell renovation or preventing the degeneration of the tissues forming the skin; however, their efficacy in preventing or treating facial wrinkles caused by muscle contraction is limited. There is therefore a need to develop new active ingredients with proven efficacy for the preparation of a cosmetic or dermopharmaceutical composition to reduce and/or eliminate facial wrinkles, especially expression wrinkles.

Expression wrinkles are considered to be those which are a result of the stress exerted by the contractions of the facial muscles responsible for producing facial expressions on the skin of the face. Expression wrinkles are usually located on the forehead, in the space between the eyebrows, around the mouth and/or around the eyes. Depending on the shape of the face, the frequency of the expressions and the existence of tics (convulsive movements which are frequently repeated and are caused by the involuntary contraction of one or several muscles, in this case, of the face), expression wrinkles can even appear in adolescence. External factors such as exposure to sun can emphasize their depth and visibility.

Botulinum toxins have been widely used with the aim of reducing and/or eliminating expression wrinkles, especially serotype A (BOTOX® Cosmetic, Allergan) [Carruthers J. D. and Carruthers J. A. (1992) *Treatment of glabellar frown lines with C. botulinum-A exotoxin, J. Dermatol. Surg. Oncol.* 18, 17-21; Mendez-Eastman S. K. (2003) *BOTOX: a review, Plast. Surg. Nurs.* 23, 64-69]. However, botulinum toxins have important drawbacks such as the requirement of their application by a doctor by means of an injection, as well as the occurrence of an immune response involving a decrease in the efficacy of the treatment over time.

The cosmetic industry has carried out important efforts to develop compounds imitating the action of botulinum toxins in the treatment and prevention of expression wrinkles. Patent application EP 1,180,524 of Lipotec, S. A. describes peptides derived from the N-terminal fragment of protein SNAP-25 having an anti-wrinkle effect, because they act with a mechanism similar to that of the botulinum toxin: the inhibition of the SNARE complex, a neuronal exocytosis mediator, involves the decrease in the release of neurotransmitters. International application WO97/34620 also describes peptides derived from the amino acid sequence of protein SNAP-25, specifically from the C-terminal region, which can inhibit neuronal exocytosis. The topical application of said compounds is becoming a possible solution for the reduction and/or elimination of expression wrinkles.

Other methods described for the reduction and/or elimination of expression wrinkles involves the use of calcium channel antagonists, particularly salts of manganese (FR 2,809, 005) or alverine (FR2,798,590), chloride channel agonists such as glycine (EP 0,704,210) or Iris pallida extracts (FR 2,746,641), certain secondary or tertiary amines (FR 2,845, 288 and FR 2,847,250), sapogenins (FR 2,838,344), limonoid compounds (US 2004/127,556) or boswellic acids (FR 2,850, 573).

The applicant of the present invention has determined that the peptides derived from the enkephalin sequence are effective in the reduction and/or elimination of facial wrinkles, especially expression wrinkles, acting by means of mechanisms different from those known in the state of the art.

Up until now, the cosmetic or dermopharmaceutical application of enkephalins has been limited to: patent application FR 2,735,687 describes the topical use of enkephalins and their derivatives as compounds with slimming capacity due to their lypolytic activity, whereas patent application FR 2,857, 588 describes the topical use of sequences derived from endorphin, including several enkephalin derivatives, to improve the skin barrier function, as well as to improve skin hydration and luminosity or to prevent the effect of atmospheric pollution on the skin.

None of the patents described previously relates to the use of enkephalins as anti-wrinkle agents, or specifically to the use of enkephalin-derived peptides for the reduction and/or elimination of expression wrinkles.

Enkephalins are a family of peptides derived from β-endorphins which can inhibit neuronal activity [Kieffer, B. L. and Gavériaux-Ruff, C. (2002) *Exploring the opioid system by gene knockout* (2002) *Prog. Neurobiol.* 66, 285-306]. The specific interaction of these peptides with their neuronal receptors causes a metabolic change in the neurons, which causes a decrease in neuronal activity. Although the action mechanism is currently being investigated, it is known that enkephalins can indirectly modulate the activity of voltage-dependent ion channels, especially the selective K⁺ channel. [Faber, E. S. and Sah, P. (2004) *Opioids inhibit lateral amygdala pyramidal neurons by enhancing a dendritic potassium current. J. Neurosci.* 24, 3031-3039]. From the point of view of action mechanism, the binding of the enkephalin to its active receptor activates a trimeric G protein complex, causing the release of $Ca^{2+}$ from intracellular reserves through the inositol phosphate receptor. Cytosolic calcium acts as an intracellular messenger triggering the activation of signaling pathways involving kinase and phosphatase proteins which chemically modify cellular proteins including ion channels. The modification of ion channels modifies their function; for example, enkephalins activate K⁺ currents in neurons causing a hyperpolarizing effect. The result of this hyperpolarization is a reduction in $Ca^{2+}$ cation-dependent neuronal exocytosis, which in turn, decreases the communication in neuronal synapses.

The overall end result is a reduction in the excitability of neuronal synapses as a result of lower neurotransmitter release [Bergevin, A., Girardot, D., Bourque, M. J. and Trudeau, L. E. (2002) *Presynaptic mu-opioid receptors regulate a late step of the secretory process in rat ventral tegmental area GABAergic neurons. Neuropharmacology,* 42, 1065-1078]. Therefore, an action of enkephalins is neurosecretion inhibition by a mechanism which is different from that described for botulinum toxin and peptides imitating the action of the latter. As a result, and like botulinum toxin and neuronal exocytosis inhibiting peptides, enkephalins also block $Ca^{2+}$ cation-dependent neuronal exocytosis.

Patent application FR 2,846,885 describes the synergistic effect of the combination of neuronal exocytosis inhibiting peptides, such as those described in patent applications EP 1,180,524 and WO97/34620, together with calcium channel inhibitors. Said invention is restricted to calcium channel inhibitors acting at the membrane level by inhibiting the entrance of calcium, or to compounds acting from inside the neurons, either releasing the intracellular reserves of calcium, or inhibiting the formation of the calcium-calmodulin complex. A person skilled in the art could not deduce the existence of a synergism in the anti-wrinkle effect when neuronal exocytosis inhibiting peptides derived from the SNAP-25 sequence and enkephalins are combined, because the latter act indirectly on potassium channels and not on sodium channels.

DESCRIPTION OF THE INVENTION

The present invention provides a simple, effective and risk-free solution for the reduction and/or elimination of facial wrinkles, preferably expression wrinkles, comprising the application on the face of a cosmetic or dermopharmaceutical composition containing at least one peptide of general formula (I).

Therefore, a first aspect of this invention relates to a cosmetic or dermopharmaceutical composition with a facial wrinkle reducing and/or eliminating activity containing a cosmetically or dermopharmaceutically effective amount of at least one peptide according to the general formula (I)

or of its cosmetically or dermopharmaceutically acceptable salts, wherein:

X and Y can be: any of the encoded natural amino acids in their L- or D-form or non-encoded amino acids;

$R_1$ can be: H or alkyl, aryl, aralkyl or acyl group; and $R_2$ can be: amino, hydroxy or thiol, all of them substituted or non-substituted with aliphatic or cyclic groups.

The preferred structures of the peptides represented in the general formula (I) are those wherein:

X can be: glycyl, D-alanyl or D-seryl;

Y can be: L-leucyl or L-methionyl $R_1$ can be: H or saturated or unsaturated, branched or cyclic, linear $C_2$ to $C_{24}$ acyl; and $R_2$ can be: amino or hydroxy, substituted or non-substituted with saturated or unsaturated, branched or cyclic, linear $C_1$ to $C_{24}$ aliphatic groups.

The preferred structures of peptides of general formula (I) are pure isomers, i.e., enantiomers or diastereoisomers.

In the context of the present invention, the term "non-encoded amino acids" relates to those amino acids that are not encoded by the genetic code and are natural or not natural, such as for example and in a non-limiting sense, citrulline, ornithine, sarcosine, desmosine, norvaline, 4-aminobutyric acid, 2-aminobutyric acid, 2-aminoisobutyric acid, 6-aminohexanoic, 1-naphthylalanine, 2-naphthylalanine, 2-aminobenzoic acid, 4-aminobenzoic acid, cycloserine, hydroxyproline, allo-isoleucine, isonipecotic acid, isoserine, phenylglycine, statin, β-alanine, or norleucine, among others, as well as their derivatives. A list of non-natural amino acids can be found in the article "Unusual amino acids in peptide synthesis" by D. C. Roberts and F. Vellaccio, in The Peptides, Vol. 5 (1983), Chapter VI, Gross E. and Meienhofer J., Eds., Academic Press, New York, USA.

The term "aliphatic group" relates to a cyclic or linear, saturated or unsaturated hydrocarbon group.

The term "hydrocarbon group" is used in the present invention to cover, for example, the alkyl, alkenyl, and alkynyl groups.

The term "alkyl group" relates to a linear or branched saturated hydrocarbon group, including, for example, methyl, ethyl, isopropyl, isobutyl, t-butyl, heptyl, dodecyl, hexadecyl, octadecyl, amyl, 2-ethylhexyl, 2-methylbutyl, 5-methylhexyl and the like.

The term "alkenyl group" relates to a linear or branched, unsaturated hydrocarbon group with one or more double carbon-carbon bonds, such as the vinyl group.

The term "alkynyl group" relates to a linear or branched, unsaturated hydrocarbon group with one or more triple carbon-carbon bonds.

The term "cyclic group" relates to a closed hyrdrocarbon ring, which can be classified into an alicyclic, aromatic or heterocyclic group.

The term "alicyclic group" relates to a cyclic hydrocarbon group with properties similar to aliphatic groups.

The term "aromatic group" or "aryl group" relates to a mono- or polycyclic aromatic hydrocarbon group.

The term "heterocyclic group" relates to a closed hydrocarbon group, in which one or more than one of the atoms of the ring is an element other than carbon (for example, nitrogen, oxygen, sulfur, etc.).

As understood in this technical area, the existence of a high degree of substitution is not only tolerated but recommended. Therefore, there may be substitution in the peptides of the present invention. For the purpose of simplifying the present description of the invention, the terms "group" and "block" will be used to distinguish between chemical species allowing substitution or which can be substituted ("group"), and those which do not allow substitution or which cannot be substituted ("block"). In this way, when the term "group" is used to describe a chemical substituent, the described chemical material includes both the non-substituted group and that containing the O, N or S atoms.

On the other hand, when the term "block" is used to describe a chemical compound or substituent, only non-substituted chemical material can be included. For example, the expression "alkyl group" will not only include open-chain saturated alkyl compounds, such as methyl, ethyl, propyl, isobutyl and the like, but also alkyl substituents containing other substituents known in the state of the art, such as hydroxy, alcoxy, amino, carboxyl, carboxamide, halogen atoms, cyano, nitro, alkylsulfonyl, and others. In this way, "alkyl group" includes ether, haloalkyl, alcohol, thiol, carboxyl, amine, hydroxyalkyl, sulfoalkyl, guanidine groups and others. On the other hand, the expression "alkyl block" is only limited to the inclusion of open-chain saturated alkyl substituents, such as methyl, ethyl, propyl, isobutyl and the like.

Cosmetically or dermopharmaceutically acceptable salts of the peptides of formula (I) provided by this invention are included within the scope of the present invention. The term "cosmetically or dermopharmaceutically acceptable salts" includes the salts commonly used to form metal salts or acid addition salts, either organic acid addition salts (such as for example, acetate, citrate, oleate, oxalate or gluconate, among others) or inorganic acid addition salts (such as for example chloride, sulfate, borate or carbonate among others). The nature of the salt is not critical, provided that it is cosmetically or dermopharmaceutically acceptable. The cosmetically or dermopharmaceutically acceptable salts of the peptides of formula (I) can be obtained by conventional methods, well known in the state of the art.

The synthesis of peptides of general formula (I) can be carried out according to conventional methods known in the state of the art, such as for example, solid phase peptide synthesis methods [Stewart J. M. and Young J. D. (1984) *Solid Phase Peptide Synthesis*, 2nd edition, Pierce Chemical Company, Rockford, Ill. Bodanzsky M. and Bodanzsky A. (1984) *The practice of Peptide Synthesis*, Springer Verlag, New York. Uoyd-Williams, P., Albericio, F. and Giralt, E. (1997) *Chemical Approaches to the Synthesis of Peptides and Proteins*. CRC, Boca Raton (FL, USA)], solution synthesis, a combination of solid phase synthesis and solution synthesis methods or enzymic synthesis [Kullmann W. (1980) *Proteases as catalysts for enzymic syntheses of opioid peptides J. Biol. Chem.* 255, 8234-8238]. The peptides can also be obtained by the fermentation of a bacterial strain that is modified or unmodified by genetic engineering with the aim of producing the desired sequences, or by controlled hydrolysis of proteins of animal or plant origin, preferably plant origin, which releases peptide fragments containing at least the desired sequence, such as for example the β-glucosidase of corn.

For example, a method for obtaining the peptides of general formula (I) is that in which a fragment of the peptide of general formula (I) having a free carboxyl group or a reactive derivative thereof, is reacted with a complementary fragment having an amino group with at least one free hydrogen atom, with the subsequent formation of an amide type bond, and wherein the functional groups of said fragments that do not participate in the formation of the amide type bond, if they exist, are conveniently protected with temporary or permanent protective groups.

Another example of a method for obtaining the peptides of general formula (I) is that in which a fragment of the peptide of general formula (I) having a leaving group, such as for example the tosyl group, the mesyl group and halogen groups, among others, is reacted with a complementary fragment having an amino group with at least one free hydrogen atom by means of a nucleophilic substitution reaction, and wherein the functional groups of said fragments that do not participate in the formation of the N—C bond, if they exist, are conveniently protected with temporary or permanent protective groups. Examples of protective groups, their insertion and elimination are described in the literature [Greene T. W. (1981) *Protective groups in organic synthesis*, John Wiley & Sons, New York. Atherton B. and Sheppard R. C. (1989) *Solid Phase Peptide Synthesis: A practical approach*, IRL Oxford University Pres]. The term "protective groups" also includes the polymeric supports used in solid phase synthesis.

When the synthesis is carried out completely or partially in solid phase, the following can be mentioned as solid supports to be used in the method of the invention: supports made of polystyrene, polyethylene glycol-grafted polystyrene and the like, such as for example p-methylbenzhydrylamine resins (MBNA) [Matsueda G. R. and Stewart J. M. (1981) *A p-methylbenzhydrylamine resin for improved solid-phase synthesis of peptide amides Peptides* 2, 45-50.], 2-chlorotrityl resins [(a) Barbs K., Gatos D., Kallitsis J., Papaphotiu G., Sotiriu P., Wenqing Y. and Schäfer W. (1989) Darstellung geschützter peptid-fragmente unter einsatz substituierter triphenylmethylharze Tetrahedron Lett. 30, 3943-3946. (b) Barlos K., Gatos D., Kapolos S., Papaphotiu G., Schäfer W. and Wenqing AND. (1989) Veresterung von partiell geschützten peptidfragmenten mit harzen. Einsatz von 2-chlortritylchlorid zur synthese von Leu15-gastrin I Tetrahedron Lett. 30, 3947-3951], TENTAGEL® (polyethylene glycol polymer-bound) resins and the like, which may or may not include a labile spacer such as 5-(4-aminomethyl-3,5-dimethoxyphenoxy) valeric acid (PAL) [Albericio F., Kneib-Cordonier N., Biancalana S., Gera L., Masada R. I., Hudson D. and Barany G. (1990) Preparation and application of the 5-(4-(9-fluorenyl-methyloxycarbonyl)aminomethyl-3,5-dimethoxyphenoxy)-valeric acid (PAL) handle for the solid-phase synthesis of C-terminal peptide amides under mild conditions J. Org. Chem. 55, 3730-3743], 2-[4-aminomethyl-(2,4-dimethoxyphenyl)phenoxyacetic acid (AM) [Rink H. (1987) *Solid-phase synthesis of protected peptide fragments using a trialkoxy-diphenyl-methylester resin Tetrahedron Lett.* 28, 3787-3790], Wang (Wang, S. S. (1973) *p-Alkoxybenzyl Alcohol Resin and p-Alkoxybenzyloxycarbonylhydrazide Resin for Solid Phase Synthesis of Protected Peptide Fragments J. Am. Chem. Soc.* 95, 1328-1333] and the like, allowing the deprotection and simultaneous cleavage of the compound from the polymeric support.

The cosmetic or dermopharmaceutical composition object of the present invention can be prepared by means of conventional methods known by persons skilled in the art. [Wilkinson J. B. and Moore R. J. (1982), *Harry's Cosmeticology, Longman Scientific & Technical*, London, UK].

The peptides object of the present invention have a variable water-solubility, according to the nature of the $R_1$, $R_2$, X and Y groups. Those which are not water-soluble can be solubilized in conventional cosmetically or dermopharmaceutically acceptable solvents such as for example ethanol, propanol or isopropanol, propylene glycol, glycerin, butylene glycol or polyethylene glycol. The peptides can also be previously incorporated in cosmetic or dermopharmaceutical carriers such as liposomes, milliparticles, microparticles and nanoparticles as well as in sponges, millispheres, microspheres and nanospheres, millicapsules, microcapsules and nanocapsules and liposheres.

The preparations containing the peptides of the present invention can be used in different types of formulations such as for example, and in a non-limiting sense, creams, lotions, gels, oils, liniments, serums, mousses, ointments, bars, pencils or sprays, including "leave on" and "rinse-off" formulations, and can also be incorporated by means of techniques known by persons skilled in the art to different types of solid accessories such as towelettes, hydrogels, adhesive (or non-adhesive) patches or face masks, or can be incorporated to different make-up line products such as make-up foundations, lotions, make-up removal lotions, concealers, eye shadows and lipsticks among others.

The cosmetic or dermopharmaceutical composition object of the present invention can be applied by means of subcutaneous injection, intradermal injection or by means of iontophoresis directly in the area of the face marked by wrinkles to achieve a greater penetration of the active ingredient. The preferred area for the application is the forehead area having expression wrinkles as well as the space between the eyebrows and the fine lines around the mouth and/or around the eyes.

The cosmetic or dermopharmaceutical composition claimed in the present invention can contain additional ingredients commonly used in compositions for the care and treatment of skin, such as for example and in a non-limiting sense, emulsion agents, emollients, organic solvents, skin conditioners such as for example, humectants, alpha hydroxy acids, moisturizers, vitamins, pigments or dyes, gelling polymers, thickeners, softeners, anti-wrinkle agents, agents that can reduce or treat under-eye bags, whitening or depigmentation agents, exfoliating agents, anti-aging agents, agents capturing free radicals and/or atmospheric pollution, NO-synthase inhibiting agents, anti-oxidizing agents, anti-glycation agents, agents stimulating the synthesis of dermal or epidermal macromolecules and/or able to inhibit their degradation, such as for example agents stimulating collagen synthesis, agents stimulating elastin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating the synthesis of lipids and components of the stratum corneum (ceramides, fatty acids etc.), skin relaxing agents, agents stimulating glycosaminoglycan synthesis, firming agents, anti-stretch mark agents, calming agents, anti-inflammatory agents, agents acting on capillary circulation and/or microcirculation, agents acting on cell metabolism, agents stimulating and/or inhibiting the synthesis of melanin, agents intended to improve the dermal-epidermal junction, preservatives, perfumes, chelating agents, plant extracts, essential oils, marine extracts, agents coming from biofermentation, mineral salts, cell extracts and sunscreens (organic or mineral photoprotection agents that are active against ultraviolet A and B rays), among others, provided that they are physically and chemically compatible with the rest of the components of the composition and especially with the peptides of general formula (I) contained in the composition of the present invention. The nature of said additional ingredients can be synthetic or natural, such as for example plant extracts.

An additional aspect of the present invention relates to a cosmetic or dermopharmaceutical composition containing a cosmetically or dermopharmaceutically effective amount of at least one peptide according to the general formula (I), and also a cosmetically or dermopharmaceutically effective amount of at least one extract with anti-wrinkle and/or anti-aging activity such as for example and in a non-limiting sense, *Vitis vinifera, Rosa canina, Curcuma longa, Iris pallida, Theobroma cacao, Ginkgo biloba*, or *Dunaliella salina* extracts, among others or of also at least one synthetic compound with anti-wrinkle and/or anti-aging activity as for example and in a non-limiting sense MATRIXYL® (palmitoyl pentapeptide-4) marketed by Sederma, VIALOX® (pentapeptide-3) marketed by Pentapharm, MYOXINOL™ (hydrolyzed Hibiscus Esculentus extract) marketed by Cognis, ALGISUM C® (methysilanol mannuronate) or HYDROXYPROLISILANE CN® (methylsilanol hydroxyproline aspartate) marketed by Exsymol, ARGIRELINE® (acetyl hexapeptide-8) marketed by Lipotec, KOLLAREN® (tripeptide-1) marketed by Institut Europeen of Biologie Cellulaire, $Ca^{2+}$ channel antagonists such as alverine, manganese or magnesium salts, certain secondary or tertiary amines, retinol and its derivatives, Coenzyme Q10 and its derivatives, boswellic acid and its derivatives or chloride channel agonists among others.

A preferred cosmetic or dermopharmaceutical composition is that containing at least one peptide according to the general formula (I), and at least one peptide derived from the protein SNAP-25. In the context of the present invention, the term "peptide derived from the protein SNAP-25" relates to any sequence of 3 to 30 amino acids or fragment of an amino acid sequence of the protein SNAP-25, defined by SEQ ID NO: 1, or any sequence of 3 to 30 amino acids different from SEQ ID NO: 1 due to mutation, insertion, deletion or substitution of at least one amino acid or due to degeneration of the genetic code, provided that the obtained sequence corresponds to a peptide having the activity of SNAP-25. Within the peptides derived from the amino acid sequence of SNAP-25, the preferred sequences are those derived from the N-terminal region of the protein SNAP-25, defined by SEQ ID NO: 2, more preferably from the region comprised between the residues 10 a 22 of the protein SNAP-25, defined by SEQ ID NO: 3, more specifically from the region comprised between the residues 12 to 19 of the protein SNAP-25, defined by SEQ ID NO: 4 and specifically by the region comprised between the residues 12 to 17 of the protein SNAP-25, defined by SEQ ID NO: 5.

The peptides of general formula (I) are used in the cosmetic or dermopharmaceutical composition of the present invention at cosmetically or dermopharmaceutically effective concentrations to achieve the desired effect; preferably between 0.000001% (by weight) and 20% (by weight); preferable between 0.00001% (by weight) and 10% (by weight) and more specifically between 0.0001% (by weight) and 5% (by weight).

Therefore, an additional aspect of this invention relates to the use of at least one peptide of general formula (I) in the manufacture of a cosmetic or dermopharmaceutical composition for its application in the skin, preferably in the skin of the face, and more specifically to reduce and/or eliminate facial wrinkles, preferably expression wrinkles.

Another aspect of the present invention relates to a cosmetic or dermopharmaceutical method for reducing and/or eliminating facial wrinkles, comprising the application in the skin of the face of a cosmetic or dermopharmaceutical composition containing at least one peptide of general formula (I) or the cosmetically or dermopharmaceutically acceptable salts thereof.

A preferred cosmetic or dermopharmaceutical method is that in which the application is carried out in those areas of the face or the forehead marked with expression wrinkles, preferably on the wrinkles around the mouth and/or the eyes, and/or on forehead wrinkles and/or on the wrinkles in the space between the eyebrows.

EXAMPLES

The following specific examples provided herein are useful for illustrating the nature of the present invention. These examples are included solely for illustrative purposes and must not be interpreted as limitations to the invention claimed herein.

General Methodology
Chemical Synthesis

All the synthetic processes are carried out in polypropylene syringes equipped with porous polyethylene disks. All the reagents are solvents are of a quality for synthesis and are used without any additional treatment. The elimination of the Fmoc group is carried out with piperidine-DMF (2:8, v/v) (1×1 min, 1×5 min; 5 mL/g resin) [Lloyd-Williams, P., Albericio, F. and Giralt, E. (1997) *Chemical Approaches to the Synthesis of Peptides and Proteins*. CRC, Boca Raton (FL, USA)]. The washings between the steps of deprotection, coupling and once again deprotection have been carried out with DMF (3×1 min) using 10 mL of solvent/g of resin. The coupling reactions have been carried out with 3 mL of solvent/g of resin. The control of the couplings is carrid out by means of the ninhydrin test [Kaiser, E., Colescott R. L., Bossinger C. D. and Cook P. (1970) *Color test for detection of free terminal amino groups in the solid-phase synthesis of peptides Anal. Biochem.* 34, 595-598]. All the synthetic transformations and washings have been carried out at 25° C.

The chromatographic analysis by HPLC was carried out in a Shimadzu equipment (Kyoto, Japan) using a reversed-phase column thermostatted at 30° C. (250×4.0 mm, Kromasil $C_8$, 5 µm, Akzo Nobel, Sweden). The elution was carried by means of a gradient of acetonitrile (+0.07% TFA) in water (+0.1% TFA) at a flow of 1 mL/min and the detection is carried out at 220 nm.

Abbreviations:

The abbreviations used for the amino acids follow the rules of the IUPAC-IUB Commission on Biochemical Nomenclature specified in *Eur. J. Biochem.* (1984) 138, 9-37 and in *J. Biol. Chem.* (1989) 264, 633-673.

BoNT A, botulinum toxin serotype A; DCM, dichloromethane; DIEA, N,N-diisopropylethylamine; DIPCDI, N,N'-diisopropylcarbodiimide; DMEM, Dulbecco's Modified Eagle's Medium; DMF, N,N-dimethylformamide; ES-MS, electrospray mass spectrometry; Fmoc, fluorenylmethoxycarbonyl; HEPES, 4-(2-hydroxyethyl)piperazine-1-ethanesulfonic acid; HOBt, 1-hydroxybenzotriazole; HPLC, high performance liquid chromatography; MeCN, acetonitryl; MeOH, methanol; NGF, nerve growth factor; Palm, palmitoyl; RNA, ribonucleic acid; tBu, tert-butyl; TFA, trifluoroacetic acid; THF, tetrahydrofuran.

Example 1

Obtaining H-Tyr-Gly-Gly-Phe-Leu-OH 3.15 g of Fmoc-L-Leu-OH (8.9 mmol, 1 equiv) dissolved in 55 mL of DCM to which 1.3 mL of DIEA (2.9 mmol, 0.33 equiv) have been added are incorporated to the dry 2-chlorotrityl resin (5.5 g, 8.8 mmol). It is left stirring for 5 minutes, after which 2.5 mL of DIEA (5.9 mmol, 0.67 equiv) are added. It is allowed to react for 40 minutes. The remaining chloride groups are protected by treatment with 4.4 mL of MeOH.

The amino terminal Fmoc group is deprotected as described in general methods and 8.52 g of Fmoc-L-Phe-OH (22 mmol, 2.5 equiv) are incorporated to the peptidyl-resin in the presence of DIPCDI (3.39 mL, 22 mmol, 2.5 equiv) and HOBt (3.37 g, 22 mmol, 2.5 equiv) using DMF as a solvent for 1 hour. The resin is subsequently washed as described in general methods and the treatment for deprotecting the Fmoc group is repeated to incorporate the next amino acid. By following the described protocols, 6.54 g of Fmoc-Gly-OH (22 mmol, 2.5 equiv) and 10.11 g of Fmoc-Tyr(tBu)—OH (22 mmol, 2.5 equiv) are coupled sequentially 2 times with the presence in each coupling of 3.37 g of HOBt (22 mmol, 2.5 equiv) and 3.39 mL of DIPCDI (22 mmol, 2.5 equiv).

The N-terminal Fmoc group is deprotected as described in general methods, the peptidyl-resin is washed with DMF (5×1 min), DCM (4×1 min), diethyl ether (4×1 min) and is dried under vacuum.

12.36 g of the dry peptidyl-resin are treated with 87 mL of TFA-$^i$Pr$_3$Si—H$_2$O (90:5:5) for 2 hours at room temperature. The filtrates are collected on cold diethyl ether (700 mL), it is filtered through porous plate and the precipitate is washed 5 times with ether (500 mL). The final precipitate is dried under vacuum.

The analysis carried out by HPLC in a gradient from 20 to 50% of MeCN (+0.07% TFA) in H$_2$O (+0.1% TFA) in 30 minutes indicated a retention time of 15.68 minutes and a purity greater than 98%. Its molecular weight was determined by ES-MS [(M+H)$^+_{theoretical}$ 556.28, (M+H)$^+_{exp}$ 556.3].

Example 2 (Prophetic)

Synthesis of Palm-Tyr-D-Ala-Gly-Phe-Met-NH$_2$ 0.685 mg of the Fmoc-AM-MBNA resin with a functionalization of 0.73 mmol/g (0.5 mmol) are treated with piperidine-DMF according to the described general protocol for the purpose of eliminating the Fmoc group. 0.93 g of Fmoc-L-Met-OH (2.5 mmol, 5 equiv) are incorporated to the unprotected resin in the presence of DIPCDI (385 µL, 2.5 mmol, 5 equiv) and HOBt (385 mg, 2.5 mmol, 5 equiv) using DMF as a solvent for 1 hour.

The resin is subsequently washed as described in the general methods and the treatment for deprotecting the Fmoc group is repeated to incorporate the next amino acid. By following the described protocols, 0.97 g of Fmoc-L-Phe-OH (2.5 mmol, 5 equiv), 0.74 g of Fmoc-Gly-OH (2.5 mmol, 5 equiv), 0.78 g of Fmoc-D-Ala-OH (2.5 mmol, 5 equiv) and 1.15 g of Fmoc-Tyr(tBu)-OH (2.5 mmol, 5 equiv) are sequentially coupled with the presence in each coupling of 385 mg of HOBt (2.5 mmol, 5 equiv) and 385 µL of DIPCDI (2.5 mmol, 5 equiv).

The N-terminal Fmoc group is deprotected as described in general methods, and 1.28 g of palmitic acid (5 mmol, 10 equiv) pre-dissolved in DMF (10 mL) are incorporated in the presence of 770 mg of HOBt (5 mmol, 10 equiv) and 770 µL of DIPCDI (5 mmol, 10 equiv). It is left reacting for 15 hours, after which the resin is washed with THF (5×1 min), DCM (5×1 min), DMF (5×1 min), MeOH (5×1 min), DMF (5×1 min), THF (5×1 min), DMF (5×1 min), DCM (4×1 min), ether (3×1 min), and is dried under vacuum.

1.00 g of the dry peptidyl-resin are treated with 15 mL of TFA-$^i$Pr$_3$Si—H$_2$O (90:5:5) for 2 hours at room temperature. The filtrates are collected on cold diethyl ether (100 mL), centrifuged for 5 minutes at 4000 rpm and the ether solution is decanted. The washings with ether are repeated 5 times. The final precipitate is dried under vacuum.

Example 3

Assay of the Activity of
H-Tyr-D-Ala-Gly-Phe-Leu-OH on Neuronal Excitability

The activity of the enkephalin-derived peptide defined by SEQ ID NO: 7 (Tyr-D-Ala-Gly-Phe-Leu) on the excitability of neurons was studied in primary cultures of rat dorsal root ganglia. These neurons were extracted following widely known methods [Nicol, G. D., Lopshire, J. C. and Pafford, C. M. (1997) *Tumor necrosis factor enhances the capsaicin sensitivity of rat sensory neurons. J. Neurosci.* 17, 975-982]. The neurons were cultured in a DMEM medium supplemented with 10% bovine serum, 5% horse serum and 50 ng/mL NGF for 2 days and the electrical activity was followed by means of a patch clamp technique with a conventional electrophysiology equipment in the current-clamp configuration [Hille, B. (2001) *Ion channels of excitable membranes. Third Ed.* Sinauer Associates, Inc]. Two neuron stimulation protocols were used to determine the inhibitory effect of the enkephalin-derived peptide defined by SEQ ID NO: 7.

Figure 1:
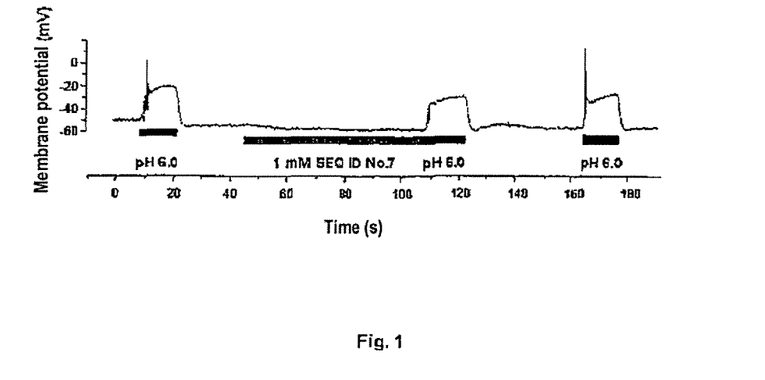
FIG. 1 illustrates membrane potentials triggered by activation of acid-dependent channels depolarizing the neuronal membrane of neurons.

The neurons were first stimulated by means of a chemical stimulus such as the exposure to a buffered solution at pH 6.0. In these conditions, acid-dependent channels depolarizing the neuronal membrane are activated, triggering action potentials (FIG. 1). The incubation of neuronal cultures with 1 mM of the enkephalin-derived peptide defined by SEQ ID NO: 7 induces the inhibition of the action potentials evoked by the exposure to an acidic extracellular medium. The inhibition of neuronal excitability caused by the enkephalin-derived peptide defined by SEQ ID NO: 7 is reversible as shown by the recovery of said excitability after eliminating the peptide from the extracellular medium. Therefore, the enkephalin-derived peptide defined by SEQ ID NO: 7 decreases the neuronal excitability caused by a chemical excitatory stimulus.

Figure 2:
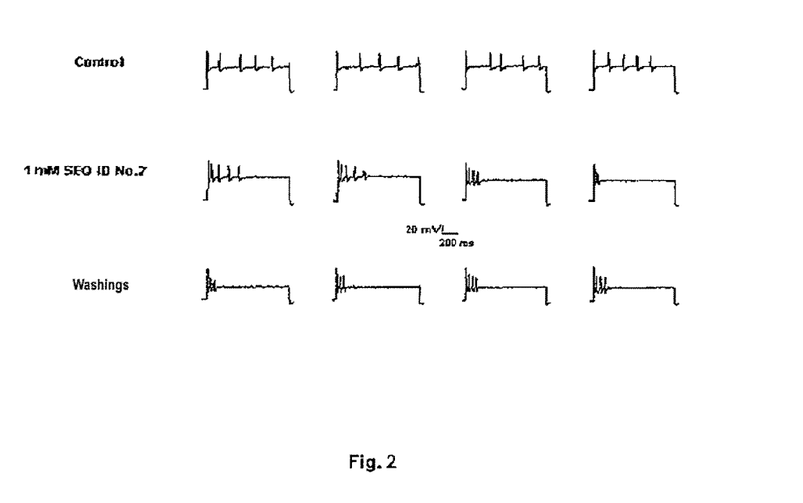
FIG. 2 illustrates the action potentials of neurons that were excited with a depolarizing electrical stimulus of 40 mV from their rest potential (control), on exposure to the enkephalin-derived peptide defined by SEQ ID NO: 7, and after washing.

Secondly, the effect of the enkephalin-derived peptide defined by SEQ ID NO: 7 on electrically evoked neuronal activity was evaluated. To that end, the neurons were excited with a depolarizing electrical stimulus of 40 mV from their rest potential. As a result, the repetitive action potentials were triggered throughout the electrical stimulation time (FIG. 2). The exposure of the neurons to 1 mM of the enkephalin-derived peptide defined by SEQ ID NO: 7 caused a decrease in the frequency and amplitude of the action potentials, indicating an inhibition thereof. This inhibition was partially reversible as indicated by the partial recovery of the action potentials. Therefore, the enkephalin-derived peptide defined by SEQ ID NO: 7 inhibits the electrically evoked nervous activity in a reversible manner.

Example 4

Assay of the Activity of the Enkephalin-Derived Peptides Defined by SEQ ID NO: 6 (Tyr-Gly-Phe-Leu) and SEQ ID NO: 7 (Tyr-D-Ala-Gly-Phe-Leu) in Calcium Channels The T-type calcium channel, isoform α1H, was recombinantly expressed in *Xenopus laevis* oocytes by means of injecting the gene encoding RNA. The activity of the ion channel was monitored by means of the voltage-clamp technique with two microelectrodes using a TEC amplifier of NPI Electronics (Germany). After 72 hours, the oocytes were transferred to an electrophysiological recording chamber, and were continuously perfused with Ringer's buffer with high Ba$^{2+}$ (80 mM NaCl, 20 mM BaCl$_2$, 3 mM KCl, 10 mM HEPES pH 7.4). The membrane potential of the ooctytes was clamped with microelectrodes to a value of −80 mV. The oocytes were electrically stimulated by means of 200 ms voltage pulses from the membrane potential of −80 mV to +80 mV in 10 mV steps. The electric currents evoked in the oocytes were recorded and were corrected with respect to leakage currents by means of a protocol of hyperpolarizing pulses to −100 mV, with a magnitude that is a fourth of the depolarizing pulses. The voltage stimulations and the data acquisition were carried out with the program PULSE/PULSEFIT of HEKA ELEKTRONIK GmbH (Germany). The calcium channel currents were first monitored in the absence of the peptides. Then the clamped oocytes were exposed to 1 mM concentrations of the peptides of SEQ ID NO: 6 and SEQ ID NO: 7 and the Ca$^{2+}$ currents were recorded in their presence. The blocking percentage was calculated as the ratio of the activated current at +80 mV in the presence of the peptide derived from the enkephalin sequence with respect to the activated current in its absence.

Figure 3:
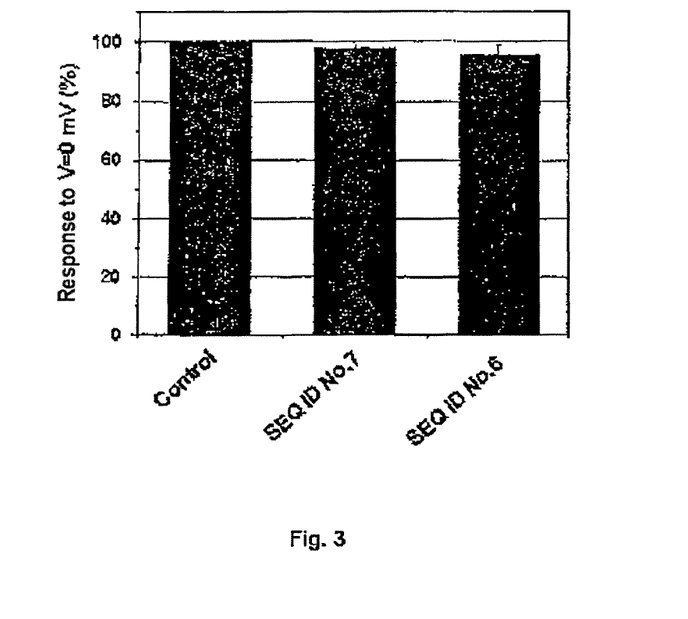
FIG. 3 illustrates the blocking percentage calculated for calcium channel currents for oocytes monitored in the absence of, and after exposure, to the peptides of SEQ ID NO: 6 and SEQ ID NO: 7.

As observed in FIG. 3, none of the two sequences directly blocked the Ca$^{2+}$ channels activated by voltage changes. In this sense, it can be concluded that the inhibition of the nervous activity by enkephalin-derived peptides was not due to the direct blocking of the calcium channels.

Example 5

Figure 4:
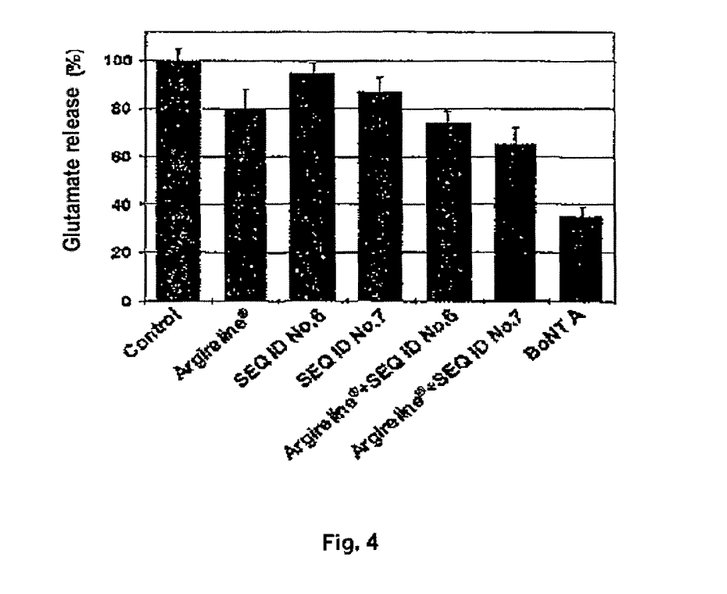
FIG. 4 illustrates electrically-evoked release of [³H]-L-glutamate by neurons in the presence of $Ca^{2+}$ and in the presence of the enkephalin-derived peptides defined by SEQ ID NO: 7, SEQ ID NO: 6, and for these peptides in combination with Argireline® (SEQ ID NO: 5).

Assay of the Activity of the Enkephalin-Derived Peptides Defined by SEQ ID NO: 6 (Tyr-Gly-Phe-Leu) and SEQ ID NO: 7 (Tyr-D-Ala-Gly-Phe-Leu) on the Neuronal Exocytosis of [$^3$H]-L-Glutamate To determine if the enkephalin-derived peptides inhibit the neuronal exocytosis of neurotransmitters, their activity on the release of the neurotransmitter L-glutamate from primary cultures of rat hippocampus neurons was monitored. The exocytosis of this neurotransmitter in neuronal cultures can be achieved by means of the electrical depolarization of the cells. The primary cultures of rat embryo hippocampus are prepared by means of conventional methods [Blanes-Mira, C., Merino, J. M., Valera, E., Fernandez-Ballester, G., Gutierrez, L. M., Viniegra, S., Pérez-Payá, E. and Ferrer-Montiel, A. Small peptides patterned after the N-terminus domain of SNAP25 inhibit SNARE complex assembly and regulated exocytosis. J. Neurochem. 88, 124-135] and are maintained in culture for 14 days in an incubator at 37° C. and 5% $CO_2$. The cultures are incubated with [$^3$H]-L-glutamine to load them with [$^3$H]-L-glutamate for 3 hours at 37° C. The excess [$^3$H]-L-glutamine is then washed and they are incubated with 1 mM of the peptides to be studied for 1 hour at 37° C. The release of [$^3$H]-L-glutamate is carried out by means of depolarization with 75 mM KCl and 2 mM $CaCl_2$ buffered in physiological buffer for 10 minutes at 37° C. The culture medium is collected and the amount of [$^3$H]-L-glutamate is quantified in a beta radioactivity counter. The results are standardized with respect to the release of [$^3$H]-L-glutamate in the absence of the peptide and are corrected with respect to the baseline release in the absence of calcium. As can be seen in FIG. 4, in the presence of the enkephalin-derived peptide defined by SEQ ID NO: 7 the exocytosis of [$^3$H]-glutamate was inhibited by 12%, indicating that the compound is a neuronal exocytosis inhibitor. The incubation with the enkephalin-derived peptide defined by SEQ ID NO: 6 caused a 4% inhibition.

In order to determine if the activity of enkephalin-derived peptides is additive and/or synergistic with the exocytosis inhibiting peptide Argireline®, defined by SEQ ID NO: 5, the potency of both peptides for separately and jointly inhibiting the electrically evoked release of [$^3$H]-L-glutamate in the presence of $Ca^{2+}$ was compared. As shown in FIG. 4, the exposure of the neurons to 1 mM of Argireline® inhibited the exocytosis of [$^3$H]-L-glutamate by 18%. The co-incubation of the cultures with 1 mM Argireline® and 1 mM of the enkephalin-derived peptide defined by SEQ ID NO: 7 inhibited the exocytosis of [$^3$H]-L-glutamate by 37%, and the co-administration of 1 mM Argireline® and 1 mM of the enkephalin-derived peptide defined by SEQ ID NO: 6 blocked the release of [$^3$H]-L-glutamate by 22% (FIG. 4). Therefore, there is an additive/synergistic effect inhibiting the regulated exocytosis of [$^3$H]-L-glutamate of Argireline® and the enkephalin-derived peptides defined by SEQ ID NO: 6 and SEQ ID NO: 7.

Example 6

Preparation of a Cosmetic Composition Containing H-Tyr-D-Ala-Gly-Phe-Leu-OH

The following formulation was prepared as described in the present invention:
The components of Phase A are weighed in a sufficiently large reactor and the mixture is heated at 80° C. to melt the waxes. The components of Phase B are weighed in a container suitable for the entire content and are heated at 70° C. Phase A is added slowly and with intense stirring to Phase B, and then Phase C is added to the previous mixture with stirring. After the addition, it is allowed to cool with slow stirring and when the mixture is at room temperature, an aqueous solution of H-Tyr-D-Ala-Gly-Phe-Leu-OH and lecithin is added, it is homogenized and the pH is corrected with triethanolamine if necessary.

The obtained cream has a pH between 6 and 7 and a viscosity of 10,000-15,000 cps (6/50).

| INGREDIENT (INCI Nomenclature) | % BY WEIGHT |
|---|---|
| PHASE A | |
| MINERAL OIL | 8.0 |
| STEARIC ACID | 2.4 |
| CETEARYL ALCOHOL | 1.6 |
| BEESWAX | 0.8 |
| PHASE B | |
| GLYCERIN | 2.4 |
| AQUA (WATER) | 63.4 |
| PHASE C | |
| CARBOMER | 0.3 |
| TRIETHANOLAMINE | 0.9 |
| PHASE D | |
| AQUA (WATER) | 15.0 |
| H-Tyr-D-Ala-Gly-Phe-Leu-OH (0.05%) | 5.0 |
| LECITHIN | 0.4 |

Example 7

A clinical trial with 20 subjects with eye contour wrinkles ("crow's feet") using the cosmetic composition described in example 6 showed that the composition can reduce the depth of eye contour wrinkles: The subjects were instructed to apply the cosmetic composition on the eye contour area with a soft massage twice a day for four weeks. Objective measurements of the macrorelief of human skin imprints in silicone were carried out by means of topographical analysis using a confocal profilometer at time 0 and 28 days after the start of the treatment.

The quantification of the results (the standard deviation of the profile evaluated at the surface) showed a 11.6% decrease of the depth of the wrinkles.

According to a first aspect, the present invention relates to a cosmetic or dermopharmaceutical composition comprising a cosmetically or dermopharmaceutically effective amount of at least one peptide of general formula:

(I)

or of the cosmetically or dermopharmaceutically acceptable salts thereof, with a facial wrinkle reducing and/or eliminating activity, wherein:
X and Y are selected from the group formed by natural amino acids in their L- or D-form or non-encoded amino acids;
$R_1$ is selected from the group formed by H or alkyl, aryl, aralkyl or acyl group and;
$R_2$ is selected from the group formed by amino, hydroxy or thiol, all of them substituted or non-substituted with aliphatic or cyclic groups,
and at least one cosmetically or dermopharmaceutically acceptable excipient or adjuvant.

According to another important aspect, the present invention relates to a cosmetic or dermopharmaceutical composition wherein the non-encoded amino acids are selected from the group formed by citrulline, ornithine, sarcosine, phenylglycine, β-alanine or norleucine.

According to another important aspect, the present invention relates to a cosmetic or dermopharmaceutical composition wherein $R_1$ is H or saturated or unsaturated, branched or cyclic, linear $C_2$ to $C_{24}$ acyl.

According to another important aspect, the present invention relates to a cosmetic or dermopharmaceutical composition wherein $R_2$ is amino or hydroxy, substituted or non-substituted with saturated or unsaturated, branched or cyclic, linear $C_1$ to $C_{24}$ aliphatic groups.

According to another important aspect, the present invention relates to a cosmetic or dermopharmaceutical composition wherein X is glycyl, D-alanyl or D-seryl.

According to another important aspect, the present invention relates to a cosmetic or dermopharmaceutical composition wherein Y is L-methionyl or L-leucyl.

According to another important aspect, the present invention relates to a cosmetic or dermopharmaceutical composition wherein X is glycyl, $R_1$ is H, acetyl or palmitoyl and $R_2$ is amino or hydroxy, substituted or non-substituted with methyl or ethyl or dodecyl or hexadecyl groups and Y is L-leucyl.

According to another important aspect, the present invention relates to a cosmetic or dermopharmaceutical composition wherein X is D-alanyl, $R_1$ is H, acetyl or palmitoyl and $R_2$ is amino or hydroxy, substituted or non-substituted with methyl or ethyl or dodecyl or hexadecyl groups and Y is L-leucyl.

According to another important aspect, the present invention relates to a cosmetic or dermopharmaceutical composition wherein the peptide of general formula (I) is at a concentration between 0.000001% and 20% by weight.

According to another important aspect, the present invention relates to a cosmetic or dermopharmaceutical composition wherein the peptide of general formula (I) is preferably at a concentration between 0.0001% and 5% by weight.

According to another important aspect, the present invention relates to a cosmetic or dermopharmaceutical composition comprising an additional cosmetically or dermopharmaceutically effective amount of an active agent selected from the group formed by an exfoliating agent, a moisturizing agent, a depigmentation or whitening agent, a pro-pigmentation agent, an anti-wrinkle agent, an agent that can reduce and/or eliminate under-eye bags, an anti-oxidizing agent, an anti-glycation agent, an NO-synthase inhibitor, an anti-aging agent, an agent stimulating the synthesis of dermal or epidermal macromolecules and/or for preventing their degradation, an agent stimulating the proliferation of fibroblasts and/or keratinocytes or for stimulating keratinocyte differentiation, a skin relaxing agent, a firming agent, an anti-atmospheric pollution and/or anti-free radical agent, an agent acting on capillary circulation and/or microcirculation, a calming agent, an anti-inflammatory agent, an agent acting on cell metabolism, an organic or mineral photoprotection agent that is active against ultraviolet A and/or B rays, and mixtures thereof. The active agent is preferably synthetic or a plant extract.

According to another important aspect, the present invention relates to a cosmetic or dermopharmaceutical composition wherein the skin relaxing agent is a peptide containing at least one amino acid sequence derived from the amino acid sequence of the protein SNAP-25 defined by SEQ ID NO: 1.

According to another important aspect, the present invention relates to a cosmetic or dermopharmaceutical composition wherein the peptide derived from the amino acid sequence of the protein SNAP-25 has an amino acid sequence contained in the sequence SEQ ID NO: 2.

According to another important aspect, the present invention relates to a cosmetic or dermopharmaceutical composition wherein the peptide derived from the amino acid sequence of the protein SNAP-25 has as amino acid sequence contained in the sequence SEQ ID NO: 3.

According to another important aspect, the present invention relates to a cosmetic or dermopharmaceutical composition wherein the peptide derived from the amino acid sequence of the protein SNAP-25 has an amino acid sequence contained in the sequence SEQ ID NO: 4.

According to another important aspect, the present invention relates to a cosmetic or dermopharmaceutical composition wherein the peptide derived from the amino acid sequence of the protein SNAP-25 is the sequence SEQ ID NO: 5.

According to another important aspect, the present invention relates to a cosmetic or dermopharmaceutical composition wherein the peptide derived from the amino acid sequence of the protein SNAP-25 is at a concentration between 0.000001% and 20% by weight.

According to another important aspect, the present invention relates to a cosmetic or dermopharmaceutical composition wherein the peptide derived from the amino acid sequence of the protein SNAP-25 is preferably at a concentration between 0.0001% and 5% by weight.

According to another important aspect, the present invention relates to a cosmetic or dermopharmaceutical composition wherein the peptide of general formula (I) is incorporated in a cosmetically or dermopharmaceutically acceptable carrier selected from the group formed by liposomes, millicapsules, microcapsules, nanocapsules, sponges, millispheres, microspheres, nanospheres, milliparticles, liposheres, microparticles and nanoparticles.

According to another important aspect, the present invention relates to a cosmetic or dermopharmaceutical composition wherein the peptide of general formula (I) is presented in a formulation selected from the group formed by emulsions of oil and/or silicone in water, emulsions of water in oil and/or silicone, milks, lotions, gels, ointments, balms, foams, body oils, soaps, bars, pencils, sprays, creams, liniments, unguents, serums and mousses.

According to another important aspect, the present invention relates to a cosmetic or dermopharmaceutical composition wherein the peptide of general formula (I) is incorporated in solid supports selected from the group formed by towelettes, hydrogels, patches and face masks.

According to another important aspect the present invention relates, to a cosmetic or dermopharmaceutical composition wherein the peptide of general formula (I) is incorporated in make-up line products selected from the group formed by concealers, make-up foundations, lotions, make-up removal lotions, eye shadows and lipsticks.

According to an important aspect, the present invention relates to the use of the peptide of general formula (I) or the cosmetically or dermopharmaceutically acceptable salts thereof in the preparation of a cosmetic or dermopharmaceutical composition reducing and/or eliminating facial wrinkles.

According to another important aspect, the present invention relates to the use of the peptide of general formula (I) or the cosmetically or dermopharmaceutically acceptable salts thereof in the preparation of a cosmetic or dermopharmaceutical composition reducing and/or eliminating facial expression wrinkles.

According to another important aspect, the present invention relates to the use of the peptide of general formula (I) or the cosmetically or dermopharmaceutically acceptable salts thereof in the preparation of a cosmetic or dermopharmaceutical composition reducing and/or eliminating facial expression wrinkles by means of the topical application in the forehead, in the space between the eyebrows and/or in the wrinkles and fine lines around the mouth and/or around the eyes.

According to another important aspect, the present invention relates to the use of the peptide of general formula (I) or the cosmetically or dermopharmaceutically acceptable salts thereof in the preparation of a cosmetic or dermopharmaceutical composition reducing and/or eliminating facial expression wrinkles by means of the application by iontophoresis in the forehead, in the space between the eyebrows and/or in the wrinkles and fine lines around the mouth and/or around the eyes.

According to another important aspect the present invention, relates to the use of the peptide of general formula (I) or the cosmetically or dermopharmaceutically acceptable salts thereof in the preparation of a cosmetic or dermopharmaceutical composition reducing and/or eliminating facial expression wrinkles by means of the application by subcutaneous or intradermal injection in the forehead, in the space between the eyebrows and/or in the wrinkles and fine lines around the mouth and/or around the eyes.

---

The invention claimed is:

1. A method of treating facial wrinkles, comprising administering topically, intradermally or subcutaneously, a cosmetic or dermopharmaceutical composition comprising:
a cosmetically or dermopharmaceutically effective amount of at least one peptide of general formula (I):

(I)

or the cosmetically or dermopharmaceutically acceptable salts thereof, wherein:
X is D-alanyl or D-seryl and Y is selected from the group consisting of natural amino acids in their L- or D-form and non-encoded amino acids,
$R_1$ is selected from the group consisting of H and alkyl, aryl, aralkyl, and acyl groups, and
$R_2$ is selected from the group consisting of amino, hydroxy, and thiol, all of them substituted or non-substituted with aliphatic or cyclic groups; and
at least a cosmetically or dermopharmaceutically acceptable excipient or adjuvant;
to the face of a subject to reduce facial wrinkles.

2. The method according to claim 1, wherein the facial wrinkles are facial expression wrinkles.

3. The method according to claim 1, wherein $R_1$ is H or saturated or unsaturated, branched or cyclic, linear $C_2$ to $C_{24}$ acyl.

4. The method according to claim 1, wherein $R_2$ is amino or hydroxy, substituted or non-substituted with saturated or unsaturated, branched or cyclic, linear $C_1$ to $C_{24}$ aliphatic groups.

5. The method according to claim 1, wherein Y is L-methionyl or L-leucyl.

6. The method according to claim 1, wherein X is glycyl, $R_1$ is H, acetyl or palmitoyl and $R_2$ is amino or hydroxy, substituted or non-substituted with methyl or ethyl or dodecyl or hexadecyl groups.

7. The method according to claim 6 wherein Y is L-leucyl.

8. The method according to claim 1, wherein X is D-alanyl, $R_1$ is H, acetyl or palmitoyl and $R_2$ is amino or hydroxy, substituted or non-substituted with methyl or ethyl or dodecyl or hexadecyl groups.

9. The method according to claim 8, wherein Y is L-leucyl.

10. The method according to claim 1, wherein the peptide of general formula (1) is at a concentration between 0.000001% and 20% by weight.

11. The method according to claim 10, wherein the peptide of general formula (1) is at a concentration between 0.0001% and 5% by weight.

12. The method according to claim 1, wherein the cosmetic or dermopharmaceutical composition comprises an additional cosmetically or dermopharmaceutically effective amount of an active agent selected from the group consisting of an exfoliating agent, a moisturizing agent, a depigmentation or whitening agent, a propigmentation agent, an anti-stretch mark agent, an anti-wrinkle agent, an anti-oxidizing agent, an anti-glycation agent, an NO-synthase inhibitor, an anti-aging agent, an agent that can reduce and/or eliminate under-eye bags, an agent stimulating the synthesis of dermal or epidermal macromolecules and/or for preventing their degradation, an agent stimulating the proliferation of fibroblasts and/or keratinocytes and for stimulating keratinocyte differentiation, a skin relaxing agent, a firming agent, an anti-atmospheric pollution and/or anti-free radical agent, an agent acting on capillary circulation and/or microcirculation, a calming agent, an anti-inflammatory agent, an agent acting on cell metabolism, an organic or mineral photoprotection agent that is active against ultraviolet A and/or B rays, and mixtures thereof.

13. The method according to claim 12, wherein the active agent is synthetic or a plant extract.

14. The method according to claim 12, wherein the skin relaxing agent is a peptide containing at least one amino acid sequence derived from the amino acid sequence of the protein SNAP-25 defined by SEQ ID NO: 1, wherein:
X and Y are selected from the group consisting of natural amino acids in their L- or D-form and non-encoded amino acids,
$R_1$ is selected from the group consisting of H and alkyl, aryl, aralkyl, and acyl groups, and
$R_2$ is selected from the group consisting of amino, hydroxy, and thiol, all of them substituted or non-substituted with aliphatic or cyclic groups.

15. The method according to claim 14, wherein the peptide derived from the amino acid sequence of the protein SNAP-25 has an amino acid sequence contained in the sequence SEQ ID NO: 2.

16. The method according to claim 15, wherein the peptide derived from the amino acid sequence of the protein SNAP-25 has as amino acid sequence contained in the sequence SEQ ID NO: 3.

17. The method according to claim 16, wherein the peptide derived from the amino acid sequence of the protein SNAP-25 has as amino acid sequence contained in the sequence SEQ ID NO: 4.

18. The method according to claim 17, wherein the peptide derived from the amino acid sequence of the protein SNAP-25 is the sequence SEQ ID NO: 5.

19. The method according to claim 14, wherein the peptide derived from the amino acid sequence of the protein SNAP-25 is at a concentration between 0.000001% and 20% by weight.

20. The method according to claim 19, wherein the peptide derived from the amino acid sequence of the protein SNAP-25 is at a concentration between 0.0001% and 5% by weight.

21. The method according to claim 1, wherein the peptide of general formula (I) is incorporated in a cosmetically or dermopharmaceutically acceptable carrier selected from the group consisting of liposomes, millicapsules, microcapsules, nanocapsules, sponges, millispheres, microspheres, nanospheres, milliparticles, lipospheres, microparticles and nanoparticles.

22. The method according to claim 1, wherein the cosmetic or dermopharmaceutical composition is presented in a formulation selected from the group consisting of emulsions of oil and/or silicone in water, emulsions of water in oil and/or silicone, milks, lotions, gels, ointments, balms, foams, body oils, soaps, bars, pencils, sprays, creams, liniments, unguents, serums and mousses.

23. The method according to claim 1, wherein the cosmetic or dermopharmaceutical composition is incorporated in solid supports selected from the group consisting of towelettes, hydro gels, patches and face masks.

24. The method according to claim 1, wherein the cosmetic or dermopharmaceutical composition is incorporated in make-up line products selected from the group consisting of concealers, make-up foundations, lotions, make-up removal lotions, eye shadows and lipsticks.

25. The method according to claim 1, wherein the administering of said composition comprises applying the composition to the forehead, to the space between the eyebrows and/or to the wrinkles and fine lines around the mouth and/or the around the eyes.

26. The method according to claim 25, wherein said composition is applied by iontophoresis or subcutaneous or intradermal injection.

27. A method of treating facial wrinkles, comprising administering a cosmetically or dermopharmaceutically effective amount of at least one peptide of general formula (I):

(I)

or the cosmetically or dermopharmaceutically acceptable salts thereof, wherein:
X is D-alanyl or D-seryl and Y is selected from the group consisting of natural amino acids in their L- or D-form and non-encoded amino acids,
$R_1$ is selected from the group consisting of H and alkyl, aryl, aralkyl and acyl groups, and
$R_2$ is selected from the group consisting of amino, hydroxy and thiol, all of them substituted or non-substituted with aliphatic or cyclic groups;
to the face of a subject to reduce facial wrinkles.

28. The method according to claim 27, wherein Y is L-methionyl or L-leucyl.

29. The method according to claim 27, wherein X is D-alanyl, $R_1$ is H, acetyl or palmitoyl, and $R_2$ is amino or hydroxy, substituted or non-substituted with methyl or ethyl or dodecyl or hexadecyl groups and, optionally, wherein Y is L-leucyl.

30. A cosmetic or dermopharmaceutical composition comprising:
a cosmetically or dermopharmaceutically effective amount of at least one peptide of general formula:

or the cosmetically or dermopharmaceutically acceptable salts thereof, wherein:
X is D-alanyl or D-seryl and Y is selected from the group consisting of natural amino acids in their L- or D-form and non-encoded amino acids,
$R_1$ is selected from the group consisting of H and alkyl, aryl, aralkyl, and acyl groups, and
$R_2$ is selected from the group consisting of amino, hydroxy, and thiol, all of them substituted or non-substituted with aliphatic or cyclic groups; and
a peptide containing at least one amino acid sequence derived from the amino acid sequence of the protein SNAP-25 defined by SEQ ID NO: 1.

31. The cosmetic or dermopharmaceutical composition according to claim 30, wherein the peptide derived from the amino acid sequence of the protein SNAP-25 has an amino acid sequence contained in a sequence selected from sequence SEQ ID NO: 2, SEQ ID NO: 3, SEQ ID NO: 4, and SEQ ID NO: 5.

* * * * *

UNITED STATES PATENT AND TRADEMARK OFFICE
CERTIFICATE OF CORRECTION

Page 1 of 1

PATENT NO. : 9,079,048 B2
APPLICATION NO. : 11/910719
DATED : July 14, 2015
INVENTOR(S) : Antonio Vicente Ferrer Montiel, Juan Cebrián Puche and Arturo Puig Montiel It is certified that error appears in the above-identified patent and that said Letters Patent is hereby corrected as shown below:

Title Page item (75) please remove:
(75) Inventors: Antonio Vincente Ferrer Montiel, Alicante (ES); Juan Cebrián Puche, Barcelona (ES); Arturo Puig Montiel, Barcelona (ES)
and replace with:
(75) Inventors: Antonio Vicente Ferrer Montiel, Alicante (ES); Juan Cebrián Puche, Barcelona (ES); Arturo Puig Montiel, Barcelona (ES)

Signed and Sealed this
Tenth Day of November, 2015

Michelle K. Lee
*Director of the United States Patent and Trademark Office*